US010786640B2

(12) United States Patent
Avitsian et al.

(10) Patent No.: US 10,786,640 B2
(45) Date of Patent: Sep. 29, 2020

(54) REVERSIBLE AIRWAY DEVICE AND RELATED METHOD FOR VENTILATING A SUBJECT

(71) Applicants: THE CLEVELAND CLINIC FOUNDATION, Cleveland, OH (US); PARKER HANNIFIN CORPORATION, Cleveland, OH (US)

(72) Inventors: Rafi Avitsian, Solon, OH (US); Andrew Zura, Beachwood, OH (US); Gino Banco, Lyndhurst, OH (US); Sean Lee, Cleveland, OH (US)

(73) Assignees: PARKER-HANNIFIN CORPORATION, Cleveland, OH (US); THE CLEVELAND CLINIC FOUNDATION, Cleveland, OH (US)

( * ) Notice: Subject to any disclaimer, the term of this patent is extended or adjusted under 35 U.S.C. 154(b) by 311 days.

(21) Appl. No.: 15/573,536

(22) PCT Filed: May 16, 2016

(86) PCT No.: PCT/US2016/032680
§ 371 (c)(1),
(2) Date: Nov. 13, 2017

(87) PCT Pub. No.: WO2016/187108
PCT Pub. Date: Nov. 24, 2016

(65) Prior Publication Data
US 2018/0104427 A1     Apr. 19, 2018

Related U.S. Application Data

(60) Provisional application No. 62/162,124, filed on May 15, 2015.

(51) Int. Cl.
*A61M 16/04* (2006.01)

(52) U.S. Cl.
CPC .... *A61M 16/0409* (2014.02); *A61M 16/0434* (2013.01); *A61M 16/0459* (2014.02);
(Continued)

(58) Field of Classification Search
CPC ............. A61M 16/04; A61M 16/0402; A61M 16/0409; A61M 16/0459; A61M 16/0475;
(Continued)

(56) References Cited

U.S. PATENT DOCUMENTS 6,167,587 B1 * 1/2001 Kasper ...................... A47L 5/30
15/320
2001/0012923 A1   8/2001 Christopher
(Continued)

FOREIGN PATENT DOCUMENTS

| CN | 104001250 A | 8/2014 |
| WO | 2009025843 A1 | 2/2009 |

(Continued)

OTHER PUBLICATIONS

International Search Report for corresponding PCT/US2016/032680 dated Jun. 10, 2016 pp. 1-18.

Primary Examiner — Samchuan C Yao
Assistant Examiner — Margaret M Luarca
(74) Attorney, Agent, or Firm — Tarolli, Sundheim, Covell & Tummino LLP

(57) ABSTRACT

One aspect of the present disclosure relates to a reversible airway device. The reversible airway device (10) can include: a supra-glottic airway support (12) comprising a multi-lumen tubular guide (14) and an optional sealing member (16); an endotracheal tube (26); and at least one seal (42). The multi-lumen tubular guide has a distal end portion (18), a proximal end portion (22), a first passageway (20) extending between the distal and proximal end portions, and a second passageway (24) that is non-concentric with the first passageway and also extends between the distal and proximal end portions. The at least one seal is disposed within the first passageway, the second passageway, or both, so as to occlude the flow of a gas through the first passageway and/or the second passageway. The endotracheal tube can be inserted into the first or second passageway and can traverse the seal.

9 Claims, 8 Drawing Sheets

(52) U.S. Cl.
CPC .... *A61M 16/0475* (2014.02); *A61M 16/0477* (2014.02); *A61M 16/0486* (2014.02); *A61M 16/0488* (2013.01)

(58) Field of Classification Search
CPC .......... A61M 16/0486; A61M 16/0477; A61M 16/0434
See application file for complete search history.

(56) References Cited

U.S. PATENT DOCUMENTS

| | | | |
|---|---|---|---|
| 2001/0032646 A1 | 10/2001 | Christopher | |
| 2002/0112728 A1 | 8/2002 | Landuyt | |
| 2005/0015048 A1* | 1/2005 | Chiu ..................... | A61M 25/10 604/101.04 |
| 2005/0139220 A1 | 6/2005 | Christopher | |
| 2010/0300450 A1* | 12/2010 | Barodka ........... | A61M 16/0461 128/207.18 |
| 2013/0324798 A1 | 12/2013 | Molnar | |
| 2014/0096766 A1 | 4/2014 | Avitsian | |

FOREIGN PATENT DOCUMENTS

| | | |
|---|---|---|
| WO | 2014068558 A1 | 5/2014 |
| WO | 2016014879 A1 | 1/2016 |

* cited by examiner

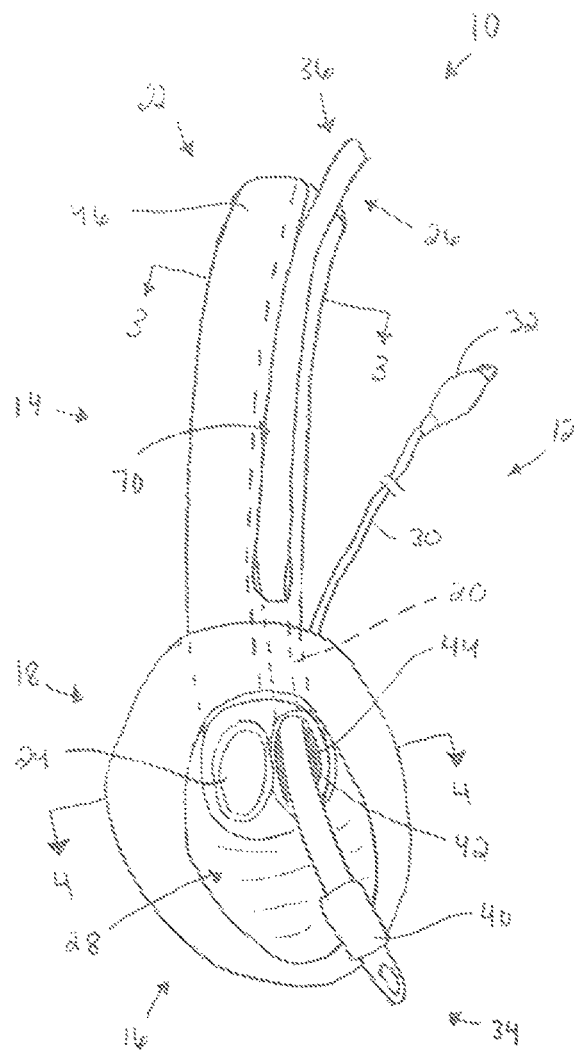
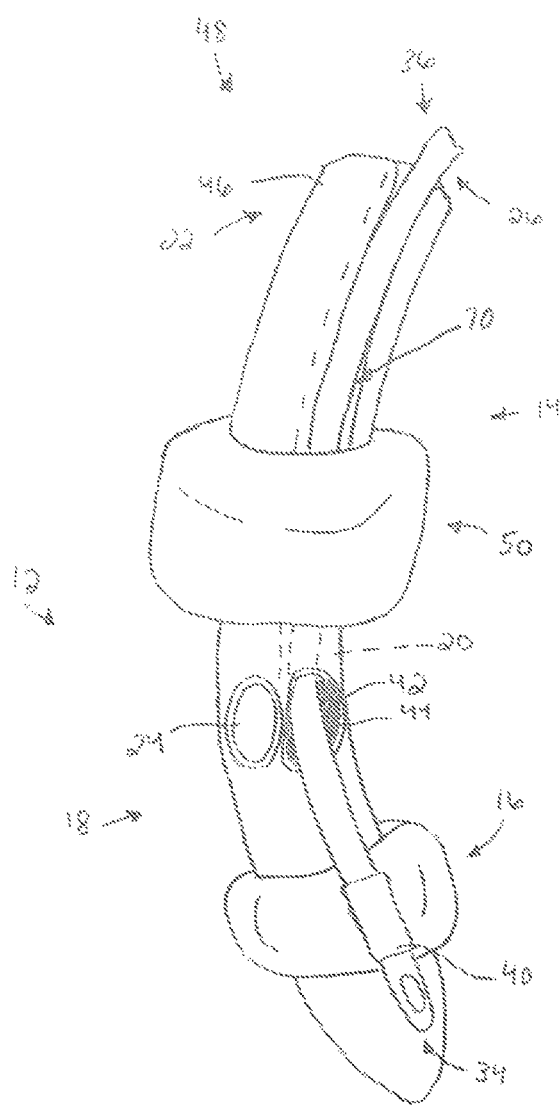
Fig. 1
Fig. 2

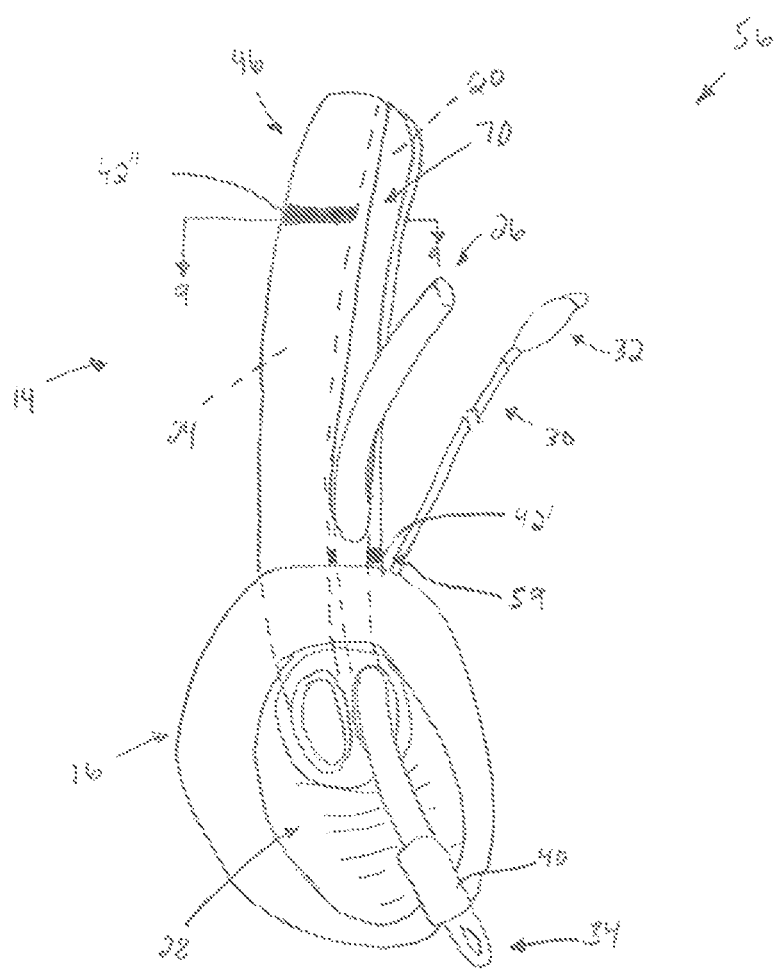

REVERSIBLE AIRWAY DEVICE AND RELATED METHOD FOR VENTILATING A SUBJECT

RELATED APPLICATION

This application claims the benefit of U.S. Provisional Patent Application Ser. No. 62/162,124, filed May 15, 2015, the entirety of which is hereby incorporated by reference for all purposes.

GOVERNMENT FUNDING

This invention was made with government support under HL074896, HL089052, HL096619 and HV058159 awarded by the National Institutes of Health. The government has certain rights in the invention.

TECHNICAL FIELD

The present disclosure relates generally to the fields of anesthesiology, emergency medicine as well as critical care medicine and, more particularly, to reversible airway devices and related methods for ventilating a subject using the airway devices that does not risk disconnection or loss of the patient's airway during ventilation.

BACKGROUND

Airway devices are widely used in hospital surgical environments to provide respiratory assistance and ventilate patients during medical procedures. While there are a multitude of airway devices currently on the market, one popular airway device is an endotracheal tube and another is a supra-glottic support device, such as a laryngeal mask airway (LMA). While the use of these devices is widespread, there are disadvantages associated with each of these devices.

Endotracheal tubes, for example, are used to ventilate patients requiring anesthesia and/or respiratory assistance. An example of a conventional endotracheal tube is a plastic tube, which is inserted into a subject's mouth, passed down the trachea through the vocal cords, and placed in the trachea proximal (or above) the carina of the lungs. The endotracheal tube may have a cuff or balloon portion surrounding the circumference of the endotracheal tube near the distal end that rests in the subject's trachea. After the endotracheal tube has been inserted and positioned properly, the cuff may be inflated to seal against the wall of the trachea. In some cases, such as pediatric patients, positive pressure can be applied without a cuff; however, there is still a risk of aspiration or gas leakage. Once sealed, positive pressure ventilation may be used to deliver respiratory assistance and, if desired, anesthesia or other gas, gas mix, etc., to the patient though the endotracheal tube via a ventilator. The cuff provides a seal that tends to block liquids and solids from passing along the outside of the endotracheal tube between the tube and the trachea wall and entering the subject's lungs.

A LMA typically consists of a hollow tube (sometimes referred to as a tubular guide, airway tube or guide) and a laryngeal mask. The laryngeal mask of the LMA is intended to fit in the supraglottic area of the patient and to cover the two openings leading, respectively, to the esophagus and the trachea, on the one hand, and blocking the fluid path to and from the esophagus and stomach, on the other hand, thereby providing a fluid path to the trachea and lungs for ventilating the patient. The laryngeal mask may is routinely positioned without requiring direct airway visualization. The laryngeal mask may or may not have an inflatable cuff or rim area. Once the laryngeal mask is placed into the subject's mouth, the cuff can be inflated to seal against the walls of the inside of the mouth and, if positioned properly, to block flow to and from the esophagus. A flexible, membranous support material extends from the cuff to form a recessed area, e.g., a space or volume, into which a gas mix can be pumped through the tube or other instrumentality of the LMA to provide the requisite air and/or anesthesia to the patient. The tube is of relatively large diameter, as compared to the usually relatively narrower diameter passage of a conventional endotracheal tube, and such relatively large diameter facilitates gas mix and exhalant flow with relatively minimal interference, pressure drop, etc. The support material supports the cuff from the tube. Thus, the LMA can be used to supply a gas mix to the recessed area and from there to the trachea during spontaneous breathing or controlled ventilation.

In some patients who have a supraglottic airway, it may become necessary to convert to an endotracheal tube. In such patients, if ventilation begins with a supra-glottic support device (e.g., a LMA) and intubation subsequently becomes necessary, the supra-glottic support device must be removed from the patient so that an endotracheal tube can be placed or an endotracheal tube can be placed through the supraglottic airway (e.g., a LMA) using a fiberoptic bronchoscope with or without an exchange catheter. These are specialized supraglottic airway devices that are designed to facilitate introduction of an endotracheal tube through their lumen. Doing so, however, requires that the ventilation be temporarily disrupted while also increasing the risk that the patient's airway may not be recovered. Additionally, placing an endotracheal tube requires the skill of an experienced medical professional, who may not be present in all circumstances in which unexpected intubation is required. Moreover, at the current time, there are no airway devices that allow conversion of an endotracheal tube to a supraglottic support without the use of some sort of exchange catheter or disruption of ventilation.

SUMMARY

The present disclosure relates generally to the fields of anesthesiology, emergency medicine as well as critical care medicine and, more particularly, to reversible airway devices and related methods for ventilating a subject using the airway devices that does not risk disconnection or loss of the patient's airway during ventilation.

One aspect of the present disclosure relates to a reversible airway device. The reversible airway device can include a multi-lumen tubular guide and at least one seal. The multi-lumen tubular guide can have a distal end portion, a proximal end portion, a first passageway extending between the distal and proximal end portions, and a second passageway that is non-concentric with the first passageway and also extends between the distal and proximal end portions. The at least one seal can be disposed within the first passageway, the second passageway, or both, so as to occlude the flow of a gas through the first passageway and/or the second passageway.

Another aspect of the present disclosure relates to a reversible airway device. The reversible airway device can comprise a tubular guide, a sealing member, an endotracheal tube, and at least one seal. The tubular guide can have a distal end portion, a proximal end portion, and a first passageway extending between the distal and proximal end portions. The sealing member can be coupled to and extend beyond the distal end portion of the tubular guide. The sealing member can have an internal channel that is in fluid communication with the first passageway. The endotracheal tube can be slidably disposed within the first passageway. The endotracheal tube can have a second passageway that is concentric with the first passageway. The at least one seal can be disposed within the first passageway and be configured to occlude the flow of a gas through the first passageway.

Another aspect of the present disclosure can include a method for providing an artificial airway in a subject. One step of the method can include providing a reversible airway device that includes a multi-lumen tubular guide and at least one seal. The multi-lumen tubular guide can have a distal end portion, a proximal end portion, a first passageway extending between the distal and proximal end portions, and a second passageway that is non-concentric with the first passageway and also extends between the distal and proximal end portions. The at least one seal can be disposed within the first passageway, the second passageway, or both, so as to occlude the flow of a gas through the first passageway and/or the second passageway. Next, the multi-lumen tubular guide can be inserted into the subject so that an airtight seal is formed between the inflatable cuff and the airway of the subject. The endotracheal tube can then be advanced through the first passageway so that a distal end of the endotracheal tube extends through the at least one seal and is positioned below the vocal cords of the subject. The endotracheal tube can be retracted so that the distal end of the endotracheal tube is positioned above the vocal cords and proximal to the at least one seal. A flow of gas through the second passageway can be uninterrupted during the inserting and advancing steps.

Another aspect of the present disclosure can include a method for providing an artificial airway in a subject. Step (a) of the method can include providing an artificial airway in a subject. The reversible airway device can comprise a multi-lumen tubular guide and a sealing mechanism. The multi-lumen tubular guide can have a distal end portion, a proximal end portion, a first passageway extending between the distal and proximal end portions, and a second passageway that is non-concentric with the first passageway and also extends between the distal and proximal end portions. The sealing mechanism can comprise at least one seal that is operatively coupled to an actuator. At step (b), the multi-lumen tubular guide can be inserted into the subject so that an airtight seal is formed between a portion of the multi-lumen tubular guide and the airway of the subject. At step (c), the sealing mechanism can be operated, if needed, so that at least one seal is positioned within the first passageway to occlude the flow of a gas therethrough. At step (d), the sealing mechanism can be operated so that the at least one seal is positioned within the second passageway to occlude the flow of a gas therethrough. At step (e), an endotracheal tube can be advanced through the first passageway so that a distal end of the endotracheal tube is positioned below the vocal cords of the subject (e.g., after deflating a distal cuff of the endotracheal tube). At step (f), the endotracheal tube can be retracted so that the distal end of the endotracheal tube is positioned above the vocal cords. Ventilation can be continuously provided to the subject during steps (b)-(f).

Another aspect of the present disclosure can include a method for staged extubation of an indwelling endotracheal tube from a subject. The endotracheal tube can include a passageway extending between a distal end and a proximal end thereof. Step (a) of the method can comprise providing a reversible airway device including a tubular guide and a sealing member. The tubular guide can have a distal end portion, a proximal end portion, and a first passageway extending between the distal and proximal end portions. The sealing member can be coupled to the distal end portion of the tubular guide. Step (b) can include inserting the tubular guide into the subject so that the endotracheal tube extends through the first passageway and an airtight seal is formed between the sealing member and the proximal esophagus. Step (c) can include withdrawing the endotracheal tube from the subject. A flow of gas through the passageway of the endotracheal tube and the first passageway can be uninterrupted during steps (b)-(c).

Another aspect of the present disclosure can include a method for staged extubation of an indwelling endotracheal tube from a subject. The endotracheal tube can include a passageway extending between a distal end and a proximal end thereof. Step (a) of the method can include providing a reversible airway device that includes a multi-lumen tubular guide and at least one seal, the multi-lumen tubular guide having a distal end portion, a proximal end portion, a first passageway extending between the distal and proximal end portions, and a second passageway that is non-concentric with the first passageway and also extends between the distal and proximal end portions. The at least one seal can be disposed within the first passageway, the second passageway, or both. Step (b) can include inserting the multi-lumen tubular guide into the subject so that the endotracheal tube extends through the first passageway and an airtight seal is formed between a portion of the multi-lumen tubular guide and the proximal esophagus. Step (c) can include withdrawing the endotracheal tube from the subject. A flow of gas through the passageway of the endotracheal tube and the second passageway of the multi-lumen tubular guide can be uninterrupted during steps (b)-(c).

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 1 is a perspective view of a reversible airway device constructed in accordance with one aspect of the present disclosure;

FIG. 2 is a perspective view of a reversible airway device constructed in accordance with another aspect of the present disclosure;

FIG. 8 is a perspective view showing a reversible airway device constructed in accordance with another aspect of the present disclosure;

FIG. 9 is a cross-sectional view taken along Line 9-9 in FIG. 8;

DETAILED DESCRIPTION

Definitions

Figure 3:
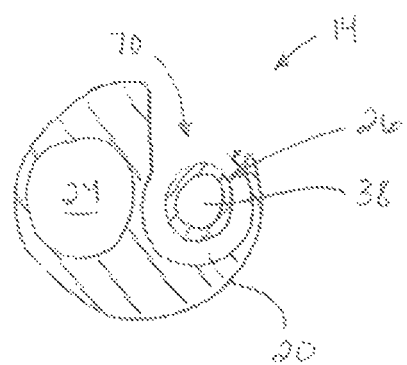
FIG. 3 is a cross-sectional view taken along Line 3-3 in FIG. 1.
Figure 4:
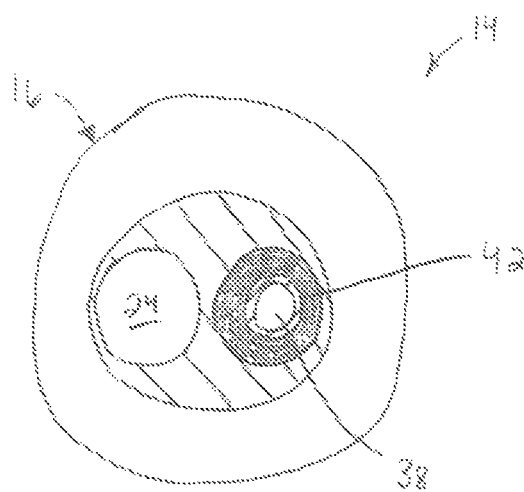
FIG. 4 is a cross-sectional view taken along Line 4-4 in FIG. 1.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the terms "ventilating" or "ventilate" can refer to providing breathable air or oxygen, for example, and removing gas, etc., e.g., exhalant exhaled by a subject, and providing anesthesia and/or other materials to and/or from the lungs of a subject. The terms can also have the usual meaning as used in the field of medicine. The various gases, e.g., oxygen, air, anesthesia, etc., alone or in combination sometimes are referred to below collectively as a gas mixture.

As used herein, the terms "subject" and "patient" can be used interchangeably and refer to any warm-blooded organism including, but not limited to, human beings, pigs, rats, mice, dogs, goats, sheep, horses, monkeys, apes, rabbits, cattle, etc.

Overview

The present disclosure relates generally to the fields of anesthesiology, emergency medicine as well as critical care medicine and, more particularly, to reversible airway devices and related methods for ventilating a subject using the airway devices that does not risk disconnection or loss of the patient's airway during ventilation. Existing airway devices and associated methods for ventilating subjects involve the introduction of an endotracheal tube through a supra-glottic airway support device. This is time consuming, involves multiple devices, entails ventilation stoppage, and requires a high level of medical expertise. Advantageously, the present disclosure integrates both sub-glottic and supra-glottic support components that can easily and automatically provide intubation and, when needed, be quickly changed to function as a supra-glottic airway support while not compromising ventilation.

FIGS. 1-11D illustrate reversible airway devices according to different aspects of the present disclosure. Certain components or features of the reversible airway devices are common to each of the airway devices and, thus, will only be described once. Certain features or components of the reversible airway devices 10 are present in the reversible airway devices disclosed in U.S. patent application Ser. No. 14/048,343 ("the '343 application") to Avitsian et al., filed Oct. 8, 2013, and U.S. Provisional Patent Application Ser. No. 62/028,886 ("the '886 application") to Avitsian et al., filed Jul. 25, 2014. Components or features that are the same between the airway devices will use the same reference numbers, whereas components or features that are different will use different reference numbers.

Reversible airway devices of the present disclosure can generally include a supra-glottic airway support (e.g., comprising a multi-lumen tubular guide and an optional sealing member, such as an inflatable cuff), an endotracheal tube, and at least one seal. By "reversible", it is meant that an artificial airway provided by the supra-glottic airway support can be readily exchanged for an artificial airway provided by the endotracheal tube without removing or disconnecting any component(s) of the airway devices, and while maintaining continuous, uninterrupted ventilation. In other words, the term "reversible" can refer to the ability of the airway devices to be automatically changed from a supra-glottic airway support to an endotracheal tube, and then back to a supra-glottic airway support, without compromising ventilation. As discussed in more detail below, the airway devices of the present disclosure can be used for all indications of a supra-glottic airway support device where there is a possibility that endotracheal intubation may be necessitated (e.g., in trauma or critically ill patients).

One example of a reversible airway device 10 is shown in FIG. 1. One component of the airway device 10 can include a supra-glottic airway support 12. The supra-glottic airway support 12 can include a multi-lumen tubular guide 14 and a sealing member 16 that surrounds, and is connected to, a distal end portion 18 of the multi-lumen tubular guide. In some instances, the sealing member 16 can comprise an inflatable cuff, such as a laryngeal mask. In other instances, the sealing member 16 can comprise a gel or other deformable material that is capable of obtaining a shape that allows it to seal within the oropharynx and supraglottic area. It will be appreciated that the multi-lumen tubular guide 14 may not include a sealing member 16 at all (e.g., where a very small caliber multi-lumen tubular guide is required, such as with a pediatric patient). In such instances, the distal end portion 18 of the multi-lumen tubular guide 14 may be positioned in the oropharynx.

The multi-lumen tubular guide 14 can include a first passageway 20 (FIG. 3) that extends between the distal end portion 18 and a proximal end portion 22 thereof, and a second passageway 24 that is non-concentric with the first passageway and also extends between the distal and proximal end portions. The first and second passageways 20 and 24 can be parallel (or substantially parallel) to one another such that a gas flowing through the first passageway does not contact a gas flowing through the second passageway. All or only a portion of the first and second passageways 20 and 24 can have any suitable cross-sectional shape, e.g., circular, semi-circular, ovoid, etc. For example, the first passageway 20 can have a semi-circular cross-sectional shape (FIG. 3); in other words, the first passageway can have a non-circular or U-shaped cross-sectional shape. As discussed in more detail below, the first passageway 20 of the multi-lumen tubular guide 14 is sized and dimensioned to receive an endotracheal tube 26.

The multi-lumen tubular guide 14 can additionally or optionally include a longitudinal slot 70 as disclosed in the '343 and '886 applications. In some instances, the longitudinal slot 70 can partially extend between the proximal and distal end portions 22 and 18 of the multi-lumen tubular guide 14 to provide access (by the endotracheal tube 26) to only the first passageway 20. For example, the longitudinal slot 70 can partially extends between the distal and proximal end portions 18 and 22 and be located directly over a portion of the first passageway 20 or the second passageway 24. The longitudinal slot 70 can serve as a rapid and convenient means for introducing the endotracheal tube 26 into the first passageway 20. Advantageously, the longitudinal slot 70 permits insertion of an end of the endotracheal tube 26 to a level of the multi-lumen tubular guide 14 that is lower than, or distal to, the proximal end portion 22 of the multi-lumen tubular guide while also permitting retraction of the endotracheal tube to its original position. The longitudinal slot 70 can also serve as a rapid and convenient means for introducing an airway tube (not shown) or other airway assistance component into the second passageway 24. Alternatively, the multi-lumen tubular guide 14 can have a cylindrical or tubular configuration such that the multi-lumen tubular guide is free of a longitudinal slot 70.

When in use, the proximal end portion 22 of the multi-lumen tubular guide 14 remains outside of the subject's mouth and, therefore, is accessible to a healthcare provider (e.g., physician, nurse or other individual). The proximal end portion 22 of the multi-lumen tubular guide 14 may be conveniently of any size and shape to secure a variety of attachments (not shown) to the tubular guide (e.g., a syringe, an endoscope probe, a gas mix supply connection to receive a gas mix for ventilating, anesthetizing, etc., a patient, a drainage tube, etc.).

Typically, the size and shape of the multi-lumen tubular guide 14 are selected so that the distal end portion 18 can be readily inserted into a subject's mouth and upper airway with the inflatable cuff substantially sealing the laryngeal inlet of the subject. The multi-lumen tubular guide 14 is generally J-shaped to follow the profile of a typical subject's airway through the mouth, over the tongue, and into the laryngopharynx region of the subject just above the opening to the larynx. The multi-lumen tubular guide 14 is shaped to prevent the subject's tongue and pharynx from obstructing access to the trachea. The multi-lumen tubular guide 14 can be made from one or a combination of materials, such as plastic, with sufficient strength and rigidity to keep the subject's teeth apart and to prevent the subject from biting down and collapsing the tubular guide. The multi-lumen tubular guide 14 (as well as the sealing member 16) can also be sized to accommodate a wide range of patient sizes (e.g., pediatric patients).

The sealing member 16 (e.g., a laryngeal mask) can include an opening 28 in fluid communication with the first and second passageways 20 and 24. In some instances, the opening 28 can be beveled to substantially match the angle of the subject's laryngeal inlet after insertion of the supra-glottic airway support 12 into the subject's airway. In other instances, the sealing member 16 can include a guide member (not shown), as disclosed in the '343 and '886 applications, for directing the endotracheal tube 26 at a desired angle (e.g., to substantially match the angle of the subject's laryngeal inlet).

The supra-glottic airway support 12 can further include an inflation tube 30 and an air valve 32 for inflating and deflating the sealing member 16, e.g., where the sealing member comprises an inflatable cuff. In addition, the supra-glottic airway support 12 can include a central support member (not shown in detail) that is a flexible and somewhat elastic or yielding membranous material, which generally provides support for the sealing member 16. Additionally or optionally, the sealing member 16 can include one or more suction ports (not shown). Each suction port can be in fluid communication with a vacuum or source of negative pressure (not shown). In one example, the sealing member 16 can include one or more suction ports circumferentially spaced about the perimeter thereof. The suction port(s) can be used to remove secretions or fluid from the patient's airway during use of the airway device 10.

Although not shown, it will be appreciated that the reversible airway device 10 can additionally or optionally include a stiffening mechanism as described in the '343 and '886 applications. The stiffening mechanism can be configured to allow a user to selectively adjust the position of the sealing member 16, for example, when the supra-glottic airway support 12 is implanted in the airway of a subject.

The reversible airway device 10 can additionally include an endotracheal tube 26 that is slidably disposed within the first passageway 20 of the multi-lumen tubular guide 14. By "slidably disposed", it is meant that the endotracheal tube 26 is not fixed within the first passageway 20 so that it is incapable of telescoping through the multi-lumen tubular guide 14. Rather, the term "slidably disposed" can mean that the endotracheal tube 26 is translatable along a longitudinal axis of the first passageway 20 (e.g., using tactile force). In some instances, substantially the entire length of the endotracheal tube 26 can extend through the first passageway 20.

The endotracheal tube 26 can be sized and dimensioned to ventilate a patient requiring anesthesia and/or respiratory assistance. In some instances, the endotracheal tube 26 can comprise a plastic tube that can be passed through the supra-glottic airway support 12, past the vocal cords, and lodged in the trachea proximal (or above) the lungs. The endotracheal tube 26 can include a distal end 34, a proximal end 36, and a passageway 38 that extends between the distal and proximal ends. With the endotracheal tube 26 disposed in the first passageway 20, the first passageway and the passageway 38 of the endotracheal tube are concentric or coaxial with one another. Since the multi-lumen tubular guide 14 is sized and dimensioned to receive the endotracheal tube 26, a diameter associated with the first passageway 20 can be greater than a diameter associated with the passageway 38 of the endotracheal tube.

The endotracheal tube 26 can include a cuff 40 or balloon portion surrounding the circumference of the endotracheal tube near the distal end 34 that rests in the patient's trachea. The cuff 40 can be inflated to seal against the wall of the trachea after the endotracheal tube 26 has been properly inserted into a subject. Once sealed, positive pressure ventilation may be used to provide respiratory assistance and, if desired, anesthesia or other gas, gas mix, etc., to the patient though the endotracheal tube 26 via a ventilator (not shown). The cuff 40 provides a seal that tends to block liquids and solids from passing along the outside of the endotracheal tube 26 between the tube and trachea wall and entering the patient's lungs. The endotracheal tube 26 can further include an inflation tube (not shown) and an air valve (not shown) for inflating and deflating the cuff 40. It will be appreciated that, in some instances, the endotracheal tube 26 may not include a cuff 40, e.g., where the endotracheal tube is sized and dimensioned for application to a pediatric patient.

Figure 6:
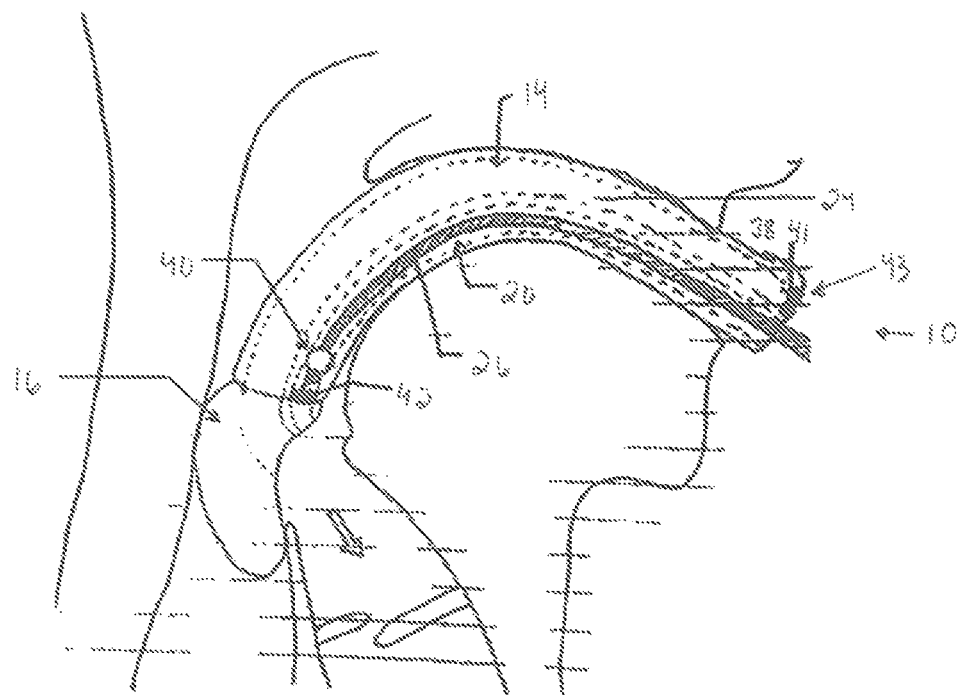

The reversible airway device 10 can also include at least one seal 42 that is disposed within the first passageway 20, the second passageway 24, or both, and is configured to occlude the flow of a gas, gas mix, etc., the first passageway and/or second passageway. In one example, the at least one seal 42 can comprise a one-way valve. As shown in FIGS. 1 and 6, a seal 42 is disposed within the first passageway 20 at a distal end 44 of the first passageway. The seal 42 is configured to prevent the flow of a gas through the first passageway 20 until the endotracheal tube 26 is inserted into the first passageway and traverses the seal, after which the gas can flow through the passageway 38 of the endotracheal tube. The seal 42 (FIG. 4) is configured to form a fluid-tight seal between an inner surface of the first passageway 20 and an outer surface of the endotracheal tube 26. It will be appreciated that the reversible airway device 10 can include at least one seal 42 as well as a second seal 41 (FIG. 6) disposed within the second passageway 24 (e.g., at a proximal end 43 of the second passageway, e.g., so that the second seal 41 is disposed within, and completely occludes, the proximal opening of the second passageway). As discussed in more detail below, the seal 42 imparts the airway device 10 with the ability to change from the supra-glottic airway support 12 to an endotracheal tube 26 (and back again) by providing a single, common airway that is not disrupted or stopped when the ventilation needs of the patient change.

Figure 5:
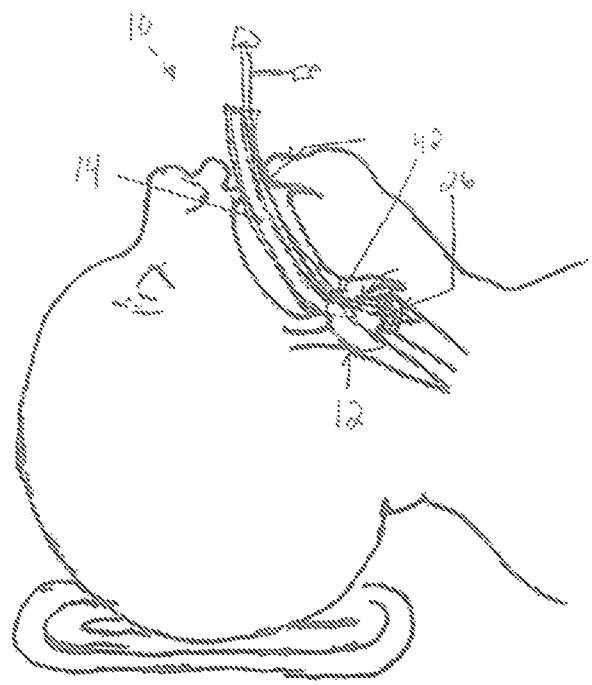
FIGS. 5-6 are schematic illustrations showing the reversible airway device in FIG. 1 being used to provide an artificial airway in a subject while an endotracheal tube of the device is positioned below (FIG. 5) and above (FIG. 6) the vocal cords.

In use, the reversible airway device 10 can be inserted into the airway of a patient using the supraglottic function of the device. In this instance, a removable ventilator connection port (not shown) can be coupled to a proximal end 46 of the second passageway 24 instead of a supraglottic lumen cap (not shown). After placement of the reversible airway device 10, a portion of the multi-lumen tubular guide 14 can be positioned to create a seal within the patient's airway. For example, the sealing member 16 can be positioned and/or manipulated (e.g., inflated) to create a seal within the patient's airway. After placement of the reversible airway device 10 and establishing ventilation of the patient, a medical professional (e.g., physician) can choose to intubate the patient by introducing the endotracheal tube 26 through the first passageway 20. Specifically, the distal end 34 of the endotracheal tube 26 can be advanced through the first passageway 20 and across the seal 42 (or simply through the opening if no seal is present) so that the distal end is positioned below the vocal cords of the subject. The cuff 40 of the endotracheal tube 26 can then be inflated to create a seal within the patient's airway (FIG. 5). Next, ventilation can be discontinued through the second passageway 24 by removing the supraglottic port, connecting it to the endotracheal tube 26, and replacing the supraglottic port with the supraglottic ventilator cap.

When intubation with the endotracheal tube 26 is no longer necessary, the cuff 40 can be deflated and the distal end 34 withdrawn into the first passageway 20 so that the distal end is located proximal to the seal 42 (FIG. 6). Since an airtight seal is still maintained between the portion of the multi-lumen tubular guide 14 (e.g., the sealing member 16) and the laryngeal outlet, ventilation of the patient can continue uninterrupted through the passageway 38 of the endotracheal tube 26 upon discontinuing ventilation. Alternatively, if there is a failure of intubation using the endotracheal tube 26, the reversible airway device 10 can be changed to the supra-glottic airway support 12 without compromising ventilation since the airtight seal is maintained.

Another example of a reversible airway device 48 is shown in FIG. 2. The reversible airway device 48 can be identically constructed as the airway device 10 in FIG. 1, except that the multi-lumen tubular guide 14 of the airway device in FIG. 2 can additionally include a second sealing member 50 (e.g., an inflatable cuff) that is axially spaced apart from, and located proximal to, the sealing member 16. Although not shown, first and second air valves can be in fluid communication (e.g., via tubing) with each of the sealing member 16 and the second sealing member 50, respectively. Where the sealing member 16 and the second sealing member 50 each comprise an inflatable cuff, the inflatable cuff and the second inflatable cuff can be selectively inflated and deflated during use of the airway device 48. For example, the inflatable cuff and the second inflatable cuff can be inflated when the airway device 48 is inserted into the upper airway of a patient to form first and second airtight seals between the inflatable cuff and the second inflatable cuff and the proximal esophagus and oropharynx of a subject (respectively).

Figure 7A:
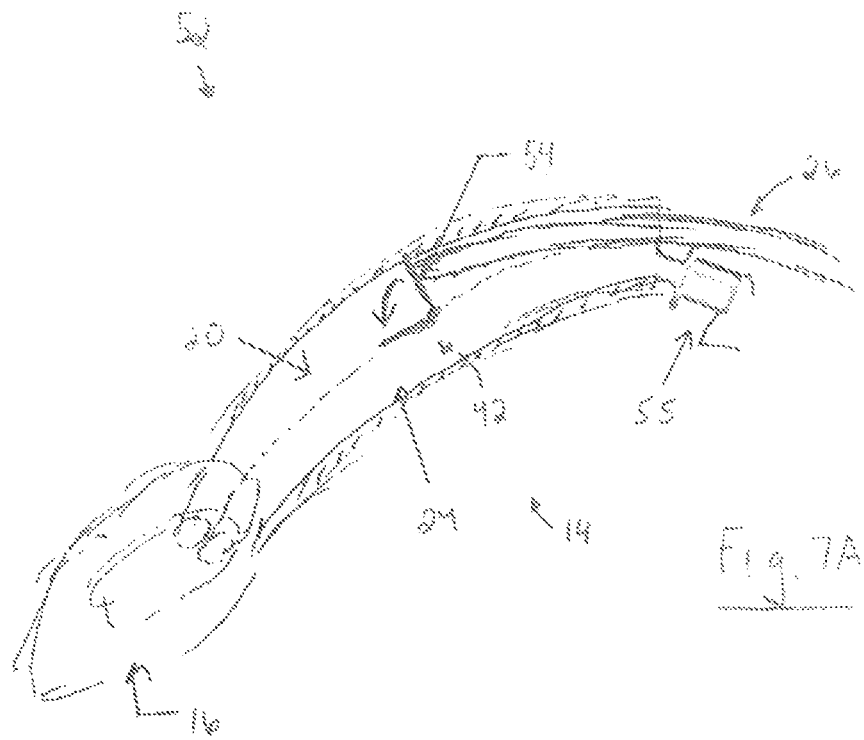
FIGS. 7A-B are schematic illustrations of a reversible airway device constructed in accordance with another aspect of the present disclosure.
Figure 7B:
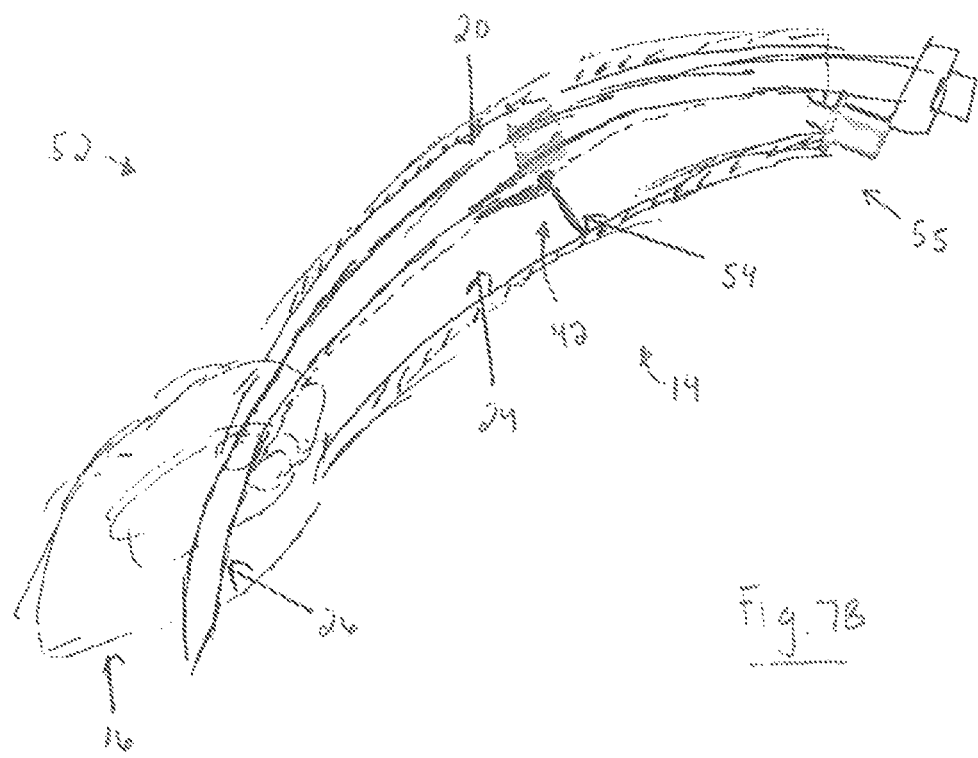

Another example of a reversible airway device 52 is shown in FIGS. 7A-B. Except as described below, the airway device 52 can be identically constructed as the airway device 10 in FIG. 1 or the airway device 48 in FIG. 2. In the airway device 52 shown in FIGS. 7A-B, the at least one seal 42 can be part of a sealing mechanism 54 that includes an actuator (not shown in detail) that is operatively coupled to the seal so that the actuator, when activated, causes the seal to rotate between the first and second passageways 20 and 24 and thereby alternatively occlude the first and second passageways. In some instances, the actuator can comprise a spring-driven hinge that is disposed on or in a common wall defining part of the first and second passageways 20 and 24.

In use, the airway device 52 can be initially placed within the airway of patient, followed by formation of an airtight seal between a portion of the multi-lumen tubular guide 14 and the airway of the patient (e.g., by inflating the sealing member 16). Following seal formation, a ventilator can be connected to the second passageway 24 via a supraglottic ventilator connector 55. At this point, the sealing mechanism 54 can be in a default configuration such that the seal 42 is located in the first passageway 20 and thereby prevents the flow of a gas therethrough, while permitting the flow of a gas through the second passageway 24. Upon a clinical decision to intubate the patient, an endotracheal tube 26 can be inserted into the first passageway 20 and, upon exerting a minimal force upon the actuator, the sealing mechanism 54 will transition to an open state. In the open state, the seal 42 can rotate to the second passageway 24 and thereby prevent the flow of gas therethrough while allowing the flow of gas through the passageway 38 of the endotracheal tube 26. The endotracheal tube 26 can then be properly positioned in the airway of the patient to provide infraglottic support.

Another example of a reversible airway device 56 is shown in FIGS. 8-9. Except as described below, the airway device 56 can be identically constructed as the airway device 10 in FIG. 1 or the airway device 48 in FIG. 2. In the airway device 56 shown in FIGS. 8-9, a first seal 42' can be disposed in the first passageway 20 at a distal end 59 thereof, and a second seal 42" can be disposed in the second passageway 24 at a proximal end 46 thereof. In use, the airway device 56 can be initially placed within the airway of patient, followed by formation of an airtight seal between a portion of the multi-lumen tubular guide 14 and the airway of the patient (e.g., by inflating the sealing member 16). Following seal formation, a supra-glottic ventilator connector can be connected to the second passageway 24 in such a way that the second seal 42" is opened to permit the flow of a gas therethrough. Alternatively, the airway device 56 can include a mechanism (not shown) that permits a user to selectively open and close the second seal 42" when ventilation through the second passageway 24 is desired. When intubation is desired, an endotracheal tube 26 can be placed into the first passageway 20, advanced across the first seal 42', and positioned so that the distal end 34 thereof is located below the vocal cords of the subject. Ventilation through the second passageway 24 can then be discontinued while ventilation through the passageway 38 of the endotracheal tube 26 is provided.

Figure 10:
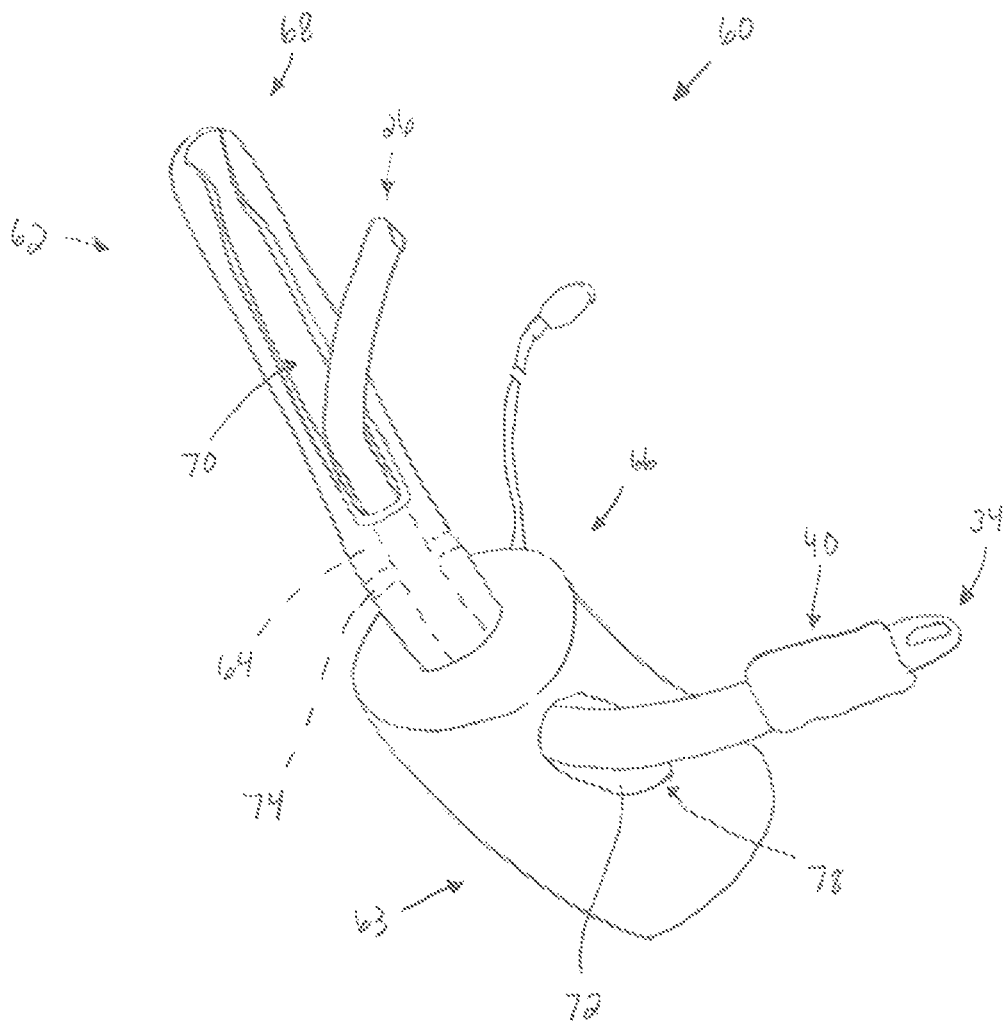
FIG. 10 is a perspective view showing a reversible airway device constructed in accordance with another aspect of the present disclosure.

Another example of a reversible airway device 60 is shown in FIG. 10. The reversible airway device 60 can comprise a tubular guide 62, a sealing member 63 (e.g., an inflatable cuff), an endotracheal tube 26, and at least one seal 42. The tubular guide 62 can be constructed in an identical or similar manner as the tubular guide disclosed in the '343 application. For example, the tubular guide 62 can include a first passageway 64 that extends between a distal end portion 66 and a proximal end portion 68 thereof. The first passageway 64 can be sized and dimensioned to receive the endotracheal tube 26. The tubular guide 62 can also include a longitudinal slot 70 as described in the '343 and '886 applications. Alternatively, the tubular guide 62 can have a cylindrical or tubular configuration such that the tubular guide is free of a longitudinal slot 70.

The sealing member 63 can be coupled to, and extend beyond, the distal end portion 66 of the tubular guide 62. The sealing member 63 can have an internal channel 72 that is in fluid communication with the first passageway 64. As shown in FIG. 10, where the sealing member 63 comprises an inflatable cuff, the sealing member can have a tubular shape when inflated. It will be appreciated, however, that other shapes are possible. Also where the sealing member 63 comprises an inflatable cuff, the inflatable cuff can include an inflation tube 30 and an air valve 32 for inflating and deflating the inflatable cuff. It will be appreciated that the sealing member 63 can alternatively be made of one or a combination of materials (e.g., a gel) that permits the sealing member to shape and seal within the oropharynx and supraglottic area.

The airway device 60 can include an endotracheal tube 26 (as described above) that is slidably disposed within the first passageway 64 of the tubular guide 62. For example, the endotracheal tube 26 can include a distal end 34, a proximal end 36, and a passageway 38 that extends between the distal and proximal ends. With the endotracheal tube 26 disposed in the first passageway 64, the passageway 38 of the endotracheal tube and the first passageway are concentric or coaxial with one another.

The airway device 60 can also include at least one seal 74 that is disposed within the first passageway 64 and configured to occlude the flow of a gas, gas mix, etc., through the first passageway. The seal 74 can be configured to permit the endotracheal tube 26 to translate along the longitudinal axis of the tubular guide 62, while simultaneously preventing a gas, gas mix, etc., to flow between the distal and proximal end portions 66 and 68 of the tubular guide. The seal 74 can be configured to form a fluid-tight seal between an inner surface of the first passageway 64 and an outer surface of the endotracheal tube 26. The seal 74 imparts the airway device 60 with the ability to change from a supra-glottic airway support 76 to an endotracheal tube 26 (and back again) by providing a single, common airway that is not disrupted or stopped when the ventilation needs of the patient change.

In one example, the seal 74 can include an O-ring, a gasket, an inflatable cuff or cushion, a one-way valve, or the like. Although the seal 74 is shown and described as being located at the distal end portion 66 of the tubular guide 62, it will be appreciated that the seal can be located at any point within the tubular guide. Additionally, it will be appreciated that two, three, or more seals 74 can be used.

Figure 11A:
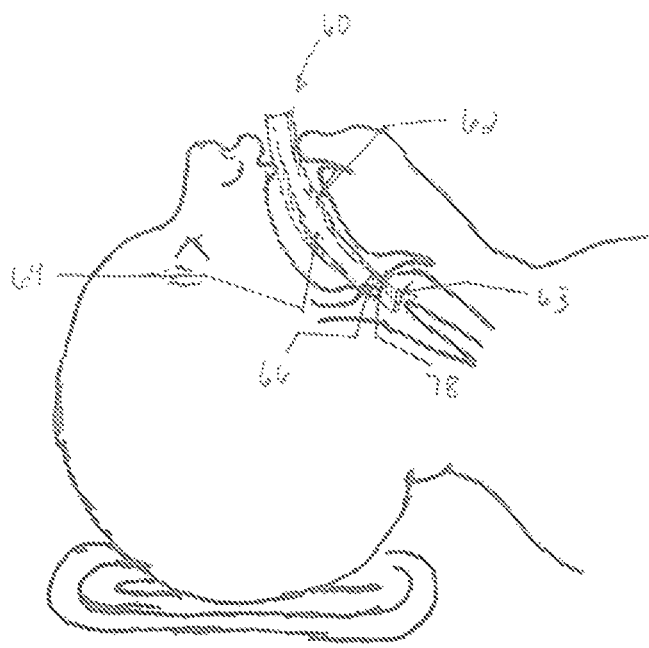
FIGS. 11A-D are a series of schematic illustrations showing the reversible airway device in FIG. 10 being used to provide an artificial airway in a subject.

Use of the airway device 60 is illustrated in FIGS. 11A-D. A patient is shown schematically with the mouth open in cross-section and leading to the back of the throat (sometimes the mouth and/or throat are referred to as the oral cavity of the patient), and from there to the trachea via the laryngeal inlet, which provides an airway that leads to the lungs. As shown in FIG. 11A, the airway device 60 can be positioned in the patient so that the sealing member 63 substantially blocks the esophagus to minimize the risk of regurgitation of stomach contents and the passage of air into the stomach. An upper portion of the sealing member 63 also guides the distal end portion 66 of the tubular guide 62 into alignment using the laryngeal inlet of the patient as a guide to insert along the patient's airway.

Figure 11B:
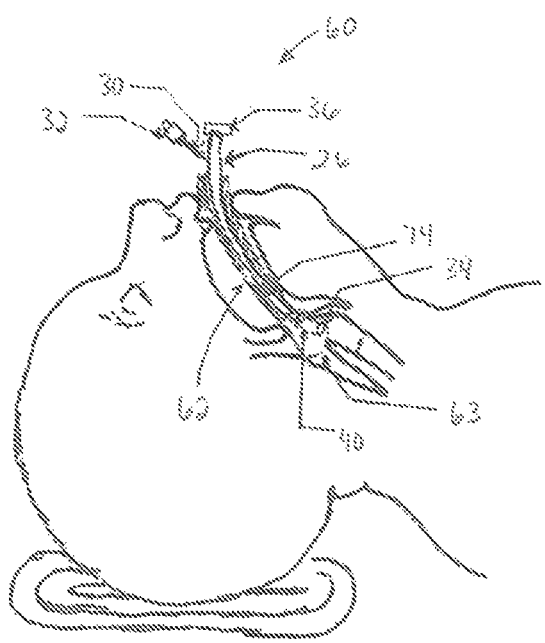

Once inserted, the sealing member 63 can be positioned and/or manipulated (e.g., inflated through the inflation tube 30) so that the sealing member substantially fills the patient's laryngopharynx at the level of the laryngeal inlet (FIG. 11B). The upper portion of the sealing member 63 can surround the laryngeal inlet so that an opening 78 of the internal channel 72 is substantially sealed in fluid communication with the laryngeal inlet, e.g., pressing against walls of the oral cavity portions of the patient. Thus, substantially all of the gas inhaled or exhaled by the patient passes through the passageway 38 of the endotracheal tube 26.

Figure 11C:
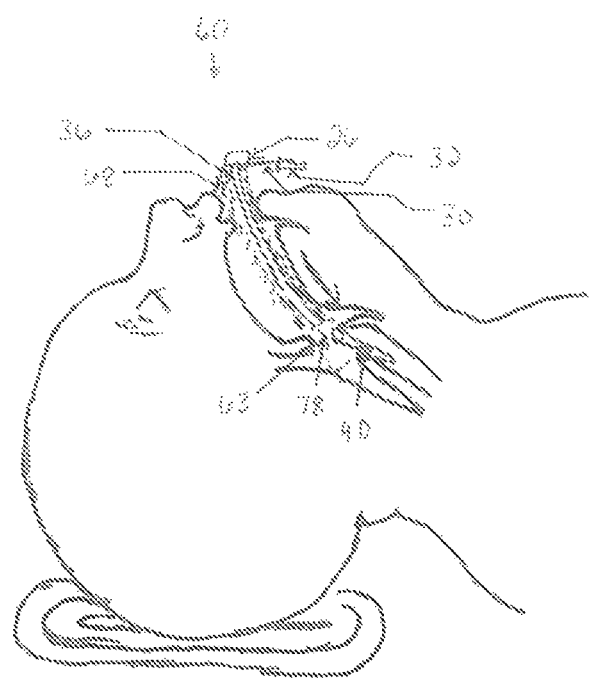
Figure 11D:
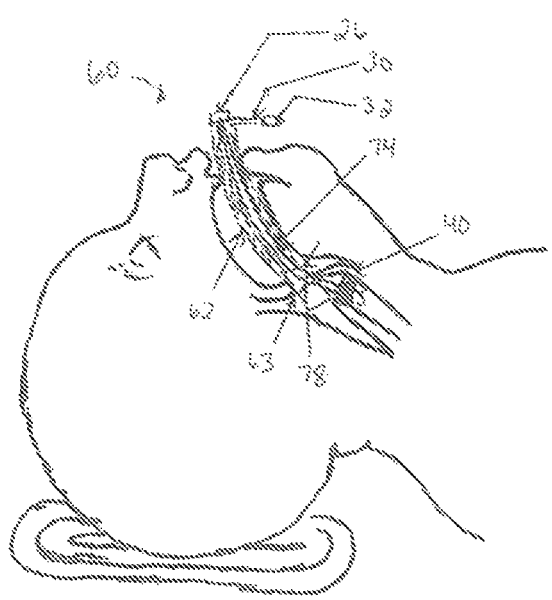

The endotracheal tube 26 of the airway device 60 can then be deployed, if necessary, as shown in FIG. 11C. The endotracheal tube 26 can be deployed automatically or under direct fiberoptic view. For example, the proximal end 36 of the endotracheal tube 26 can be urged downward through the tubular guide 62 using, for example, tactile force. As the endotracheal tube 26 is advanced, the distal end 34 emerges from the internal channel 72 of the sealing member 63 and passes through the vocal cords of the patient until the cuff 40 of the endotracheal tube is positioned distal (below) the vocal cords. Next, the cuff 40 of the endotracheal tube 26 can be inflated to seal against the wall of the trachea (FIG. 11D). Once sealed, positive pressure ventilation may be used to provide respiratory assistance and, if desired, anesthesia or other gas, gas mix, etc., to the patient though the passageway 38 of the endotracheal tube 26 via a ventilator.

When intubation with the endotracheal tube 26 is no longer necessary, the cuff 40 can be deflated and the distal end 34 withdrawn into the tubular guide 62. Since an airtight seal is still maintained between a portion of the multi-channel tubular guide 14 (e.g., the sealing member 63) and the laryngeal outlet, ventilation of the patient can continue uninterrupted through the passageway 38 upon discontinuing ventilation with the endotracheal tube 26. Alternatively, if there is a failure of intubation using the endotracheal tube 26, the airway device 60 can be changed to the supra-glottic airway support 12 without compromising ventilation since the airtight seal is maintained.

Another aspect of the present disclosure can include a method for staged extubation of a patient using a reversible airway device 10, 48, 52, and 56 comprising a multi-lumen tubular guide 14 and at least one seal 42 disposed, for example, in the first passageway 20 thereof. Examples of such airway devices 10, 48, 52, and 56 are discussed above.

One step of the method can include coupling the multi-lumen tubular guide 14 to an indwelling endotracheal tube (not shown) so that the endotracheal tube is at least partly disposed in the first passageway 20. Next, the multi-lumen tubular guide 14 can be urged into the patient's airway so that the endotracheal tube extends through the entire first passageway 20, including the seal 42, and so that the sealing member 16 of the multi-lumen tubular guide substantially blocks the esophagus. The sealing member 16 can then be positioned and/or manipulated (e.g., inflated) so that the sealing member substantially fills the patient's laryngopharynx at the level of the laryngeal inlet. The upper portion of the sealing member 16 can surround the laryngeal inlet so that the second passageway 24 is substantially sealed in fluid communication with the laryngeal inlet.

With the seal established, the cuff of the endotracheal tube can be deflated. The proximal end of the endotracheal tube can then be capped to prevent airflow through the passageway of the endotracheal tube. Airflow can then seamlessly transition from the endotracheal tube to the second passageway 24 of the multi-lumen tubular guide 14. If needed, the proximal end 46 of the second passageway 24 can be coupled with a ventilator connector to facilitate normal respiration and extubation of the patient.

Another aspect of the present disclosure can include a method for staged extubation of a patient using a reversible airway device 60 comprising tubular guide 62 with a first passageway 64 and a seal 74 disposed therein. It will be appreciated that any of the airway devices disclosed in the '343 and '886 applications may alternatively be used for staged extubation.

One step of the method can include coupling the tubular guide 62 to an indwelling endotracheal tube so that the endotracheal tube is at least partly disposed in the first passageway 64. Next, the tubular guide 62 can be urged into the patient's airway so that the endotracheal tube extends through the entire first passageway 64, including the seal 74, and the sealing member 63 of the tubular guide substantially blocks the esophagus. The sealing member 63 can then be positioned and/or manipulated (e.g., inflated) so that the sealing member substantially fills the patient's laryngopharynx at the level of the laryngeal inlet. The upper portion of the sealing member 63 can surround the laryngeal inlet so that the opening of the sealing member is substantially sealed in fluid communication with the laryngeal inlet.

When intubation with the endotracheal tube is no longer necessary, the cuff of the endotracheal tube can be deflated and the distal end withdrawn into the tubular guide 62. Since an airtight seal is still maintained between the sealing member 63 and the laryngeal outlet, ventilation of the patient can continue uninterrupted through the passageway of the endotracheal tube upon discontinuing ventilation with the endotracheal tube. The airway device 60 can then be changed to the supra-glottic airway support, without compromising ventilation, by removing the endotracheal tube completely from the tubular guide 62 since the airtight seal is maintained.

From the above description of the present disclosure, those skilled in the art will perceive improvements, changes and modifications. For example, it will be appreciated that order of steps can be changed so that the endotracheal tube 26 is deployed before supra-glottic ventilation begins. Additionally, even though certain embodiments of the reversible airway devices are described as having two non-concentric passageways, it will be appreciated that reversible airway devices of the present disclosure can have three, four, or more non-concentric passageways. Such improvements, changes, and modifications are within the skill of those in the art and are intended to be covered by the appended claims. All patents, patent applications, and publication cited herein are incorporated by reference in their entirety.

The following is claimed:

1. A reversible airway device comprising:
   a multi-lumen tubular guide having a distal end portion, a proximal end portion, a first passageway extending between the distal and proximal end portions, and a second passageway that is non-concentric with the first passageway and also extends between the distal and proximal end portions; and
   a seal disposed within the first passageway or the second passageway, so as to occlude the flow of a gas through the first passageway and/or the second passageway;
   wherein the seal is part of a sealing mechanism that includes an actuator operatively coupled to the seal so that the actuator that, when activated, causes the seal to rotate between and thereby alternatively occlude the first and second passageways.

2. The airway device of claim 1, wherein the distal end portion includes a sealing member coupled thereto.

3. The airway device of claim 1, further including a second sealing member that is axially spaced apart from, and located proximal to, the sealing member.

4. The airway device of claim 2, wherein the sealing member is an inflatable cuff.

5. The airway device of claim 4, wherein the inflatable cuff is a laryngeal mask.

6. The airway device of claim 1, wherein the multi-lumen tubular guide includes a longitudinal slot that partially extends between the distal and proximal end portions thereof and is located directly over a portion of the first passageway or the second passageway.

7. A method for providing an artificial airway in a subject, the method comprising the steps of:
(a) providing a reversible airway device that includes a multi-lumen tubular guide and a sealing mechanism, the multi-lumen tubular guide having a distal end portion, a proximal end portion, a first passageway extending between the distal and proximal end portions, and a second passageway that is non-concentric with the first passageway and also extends between the distal and proximal end portions, the sealing mechanism comprising a seal that is operatively coupled to an actuator;
(b) inserting the multi-lumen tubular guide into the subject so that an airtight seal is formed between a portion of the multi-lumen tubular guide and the airway of the subject;
(c) operating the sealing mechanism, if needed, so that the seal is positioned within the first passageway to occlude the flow of a gas therethrough;
(d) operating the sealing mechanism so that the seal is positioned within the second passageway to occlude the flow of a gas therethrough;
(e) advancing an endotracheal tube through the first passageway so that a distal end of the endotracheal tube is positioned below the vocal cords of the subject; and
(f) retracting the endotracheal tube so that the distal end of the endotracheal tube is positioned above the vocal cords;
wherein ventilation is continuously provided to the subject during steps (b)-(f).

8. A method for staged extubation of an indwelling endotracheal tube from a subject, the endotracheal tube including a passageway extending between a distal end and a proximal end thereof, the method comprising the steps of:
(a) providing a reversible airway device that includes a multi-lumen tubular guide and a seal, the multi-lumen tubular guide having a distal end portion, a proximal end portion, a first passageway extending between the distal and proximal end portions, and a second passageway that is non-concentric with the first passageway and also extends between the distal and proximal end portions, the seal being disposed within the first passageway or the second passageway;
(b) inserting the multi-lumen tubular guide into the subject so that the endotracheal tube extends through the first passageway and an airtight seal is formed between a portion of the multi-lumen tubular guide and the proximal esophagus; and
(c) withdrawing the endotracheal tube from the subject;
wherein a flow of gas through the passageway of the endotracheal tube and the second passageway of the multi-lumen tubular guide is uninterrupted during steps (b)-(c);
wherein the seal is part of a sealing mechanism that includes an actuator operatively coupled to the seal so that the actuator that, when activated, causes the seal to rotate between and thereby alternatively occlude the first and second passageways.

9. The method of claim 8, wherein after step (b), a cuff that is coupled to the distal end of the endotracheal tube is deflated.

* * * * *